United States Patent [19]

Goettsche et al.

[11] Patent Number: 5,187,194
[45] Date of Patent: Feb. 16, 1993

[54] WOOD PRESERVATIVES CONTAINING POLYMERIC NITROGEN COMPOUNDS

[75] Inventors: Reimer Goettsche, Baden-Baden; Wolfgang Reuther, Heidelberg, both of Fed. Rep. of Germany

[73] Assignee: Dr. Wolman GmbH, Sinzheim, Fed. Rep. of Germany

[21] Appl. No.: 598,080

[22] Filed: Oct. 16, 1990

[30] Foreign Application Priority Data

Oct. 20, 1989 [DE] Fed. Rep. of Germany ....... 3934935

[51] Int. Cl.[5] .................... A01N 55/02; A01N 33/24
[52] U.S. Cl. ..................: 514/499; 514/492; 514/494; 514/500; 514/501; 514/645; 514/674; 424/630; 424/632; 424/633; 424/634; 424/635; 424/637; 424/638; 424/641; 424/646; 424/78.08
[58] Field of Search ............... 514/499, 500, 674, 492, 514/494, 501, 645; 424/78.08, 630, 632, 633, 634, 635, 637, 638, 641, 646

[56] References Cited

U.S. PATENT DOCUMENTS

| | | | |
|---|---|---|---|
| 3,769,398 | 10/1973 | Hewitt | 514/556 |
| 4,038,451 | 7/1977 | Brown et al. | 428/274 |
| 4,075,394 | 2/1978 | Meyer | 428/541 |
| 4,143,153 | 3/1979 | Pommer et al. | 514/499 |

OTHER PUBLICATIONS

Chemical Abstracts 103: 25453h (1985).
Japanese Patents Gazette, Aug. 3, 1988, Nr. 88-171459/25.

Primary Examiner—Allen J. Robinson
Assistant Examiner—John D. Pak
Attorney, Agent, or Firm—Oblon, Spivak, McClelland, Maier & Neustadt

[57] ABSTRACT

Wood preservatives which contain a mixture of an N-organyldiazeniumdioxy-metal salt and a complex-forming polymeric nitrogen compound are used for preserving wood.

3 Claims, No Drawings

WOOD PRESERVATIVES CONTAINING POLYMERIC NITROGEN COMPOUNDS

The present invention relates to water-soluble wood preservatives which contain a metal salt of an N-organyldiazeniumdioxy compound and a polymeric amine.

Water-soluble wood preservatives based on complex-forming amines and bis-(N-cyclohexyldiazeniumdioxy)-copper (Cu-HDO, former name copper salt of N-nitrosocyclohexylhydroxylamine) are known (DE 2 410 603.4 and EP 234 461).

Examples of known amines are ethylenediamine, diethylenetriamine and dipropylenetriamine. In the impregnation of wood in the large scale industrial process, the pressure impregnation process, the depth of penetration and the distribution of the Cu-HDO in the wood is insufficient to ensure permanent preservation of the wood, for example in the case of roundwood, such as poles or palisades, particularly when they are used in contact with earth, for example as telegraph poles. The aqueous alkaline solutions of the complex Cu-HDO (pH about 9–10) react with the acidic wood constituents during the impregnation itself in such a way that the CuHDO is precipitated on contact with wood and the solution therefore does not penetrate deeply into the wood.

Treatment agents based on aqueous mixtures of bis-(N-cyclohexyldiazeniumdioxy)copper, polyamines (di- or triamines, such as ethylenediamine or diethylenetriamine) and complex-forming carboxylic acids (EP 234 461) penetrate well into roundwood but fixing of copper is insufficient in the case of said treatment agents; from 12 to 20% of the copper are washed out in the case of normal fixing (20° C./4 weeks) and up to 30% of the copper introduced are washed out after rapid fixing (about 100° C., from 1 to 2 hours; superheated steam).

When tartaric or lactic acid is used as the complex-forming acid, fixing of copper in the wood is better but the depth of penetration and distribution of preservative during impregnation of, for example, pine roundwood by the pressure impregnation process is not satisfactory for sufficient wood preservation.

Known complexing agents, amines and acids can be leeched out of the wood by water (precipitation, soil moisture) and can enter the environment.

Furthermore, the known amines have a measurable vapor pressure. The permitted concentrations in inspired air are, for example, 6 mg/$m^3$ in the case of ethanolamine and 4 mg/$m^3$ in the case of diethylenetriamine.

It has been found that these disadvantages do not occur if water-soluble preservatives based on mixtures of bis-(N-organodiazeniumdioxy)metal compounds with complexforming, polymer nitrogen compounds are used.

N-organodiazeniumdioxy compounds are, for example, the N-cyclohexyldiazeniumdioxy, N-$C_4$–$C_{10}$-alkyldiazeniumdioxy, in particular N-$C_5$–$C_8$-alkyldiazeniumdioxy, N-aryldiazeniumdioxy, in particular N-phenyldiazeniumdioxy, compounds and mixtures thereof. Metal salts are, for example, the copper, zinc, nickel or cobalt salts and mixtures thereof. Such compounds are, for example, bis-(N-cyclohexyldiazeniumdioxy)copper and/or -zinc and/or -nickel and/or -cobalt, bis-(N-alkyldiazeniumdioxy)copper and/or -zinc and/or -nickel and/or cobalt and bis-(N-aryldiazeniumdioxy)copper and/or -zinc and/or -nickel and/or -cobalt.

Complex-forming, polymeric nitrogen compounds are, for example, polyethyleneimines, polyamidoamines (condensates of polyamines and adipic acid), and condensates, for example those based on diethylenetriamine/triethanolamine and/or diethanolamine/diethylenetriamine. Copper and zinc compounds, polyethyleneimines and N-cyclohexyldiazeniumdioxy compounds are preferred.

Polyethyleneimines (PEI) are known and are formed by polymerization of 1,2-ethyleneimine. They contain primary (terminal group), secondary and tertiary (branching) nitrogen. Suitable polyethyleneimines are those in which n is greater than 10; very good results were obtained using PEI having a degree of polymerization n of from 50 to 1,000.

Polyamidoamines are formed, for example, by reacting diethylenetriamine with adipic acid at from 150° to 200° C.

Further condensates are formed, for example, by heating diethanolamine or triethanolamine to 200°–220° C. in the presence of phosphonic acid ($H_3PO_3$).

The penetration of aqueous solutions of the novel preservatives is not adversely affected during impregnation, for example by the pressure impregnation process: precipitation of the abovementioned metal salts on contact with the wood does not occur, the solutions penetrate thoroughly into the wood and distribution of the active ingredient in the wood meets practical requirements. Precipitation of the insoluble copper and/or zinc salts begins only after impregnation. They are thus fixed in the wood. The fixing time is dependent on the temperature. Fixing is complete at 20° C. after, for example, from 1 to 2 weeks, and the fixing reaction can be considerably accelerated by treatment with superheated steam (steam at 100° C. or higher), in which case it is complete, for example, after only from 1 to 2 hours.

The polymeric nitrogen compounds have virtually no measurable vapor pressure. They are therefore almost completely absent from the inspired air. After fixing, they are not washed out of the wood, for example by weather effects.

For example, bis-(N-cyclohexyldiazeniumdioxy)copper and/or -zinc (Cu-HDO/Zn-HDO) and/or -cobalt (Co-HDO) and/or -nickel (Ni-HDO), bis-(N-phenyldiazeniumdioxy)- or or bis-(N-tolyldiazeniumdioxy)-copper and/or -zinc and/or -cobalt and/or -nickel and bis-(N-$C_5$-$C_8$-alkyldiazeniumdioxy)copper and/or -zinc and/or -cobalt and/or -nickel and mixtures thereof can be used.

Instead, it is also possible to use the corresponding water-soluble alkali metal and/or ammonium salts together with water-soluble and/or water-insoluble metal compounds, e.g. copper acetate and/or zinc acetate, copper borate and/or zinc borate, copper oxide and/or zinc oxide, copper hydroxide and/or zinc hydroxide, zinc carbonate, basic copper carbonate and/or the corresponding nickel and/or cobalt compounds.

The wood preservatives can, if required, contain further compounds, for example a compound having a fungicidal anion, such as a boron compound, e.g. an alkali metal borate, an amine borate or boric acid, fluorides, e.g. potassium fluoride, and/or salts of fluoboric acid and/or fluorophosphoric acid and/or difluorophosphoric acid.

To improve the corrosion behavior or stabilization and to buffer to a pH of about 8–10, for example, aliphatic carboxylic acids or polycarboxylic acids may be added. Examples of suitable aliphatic carboxylic acids are $C_5-C_{20}$-monocarboxylic acids, such as hexanoic acid, heptanoic acid, octanoic acid, nonanoic acid, decanoic acid, 2-ethylpentanoic acid, 2-ethylhexanoic acid, 2-ethylheptanoic acid, isooctanoic acid, isononanoic acid, isodecanoic acid and versatic acids (highly branched monocarboxylic acids), and $C_5-C_{20}$-dicarboxylic acids, e.g. sebacic acid.

Amines, e.g. aminoethylethanolamine or dipropylenetriamine, can be added to obtain a certain pH.

Mixing with primary, secondary or tertiary fatty amines which contain one or more hydrophilic radicals of not less than 6 carbon atoms makes it possible to improve the action spectrum against wood-destroying and wood-discoloring fungi and against wood-destroying insects.

These amines are of, for example, the general formulae a) 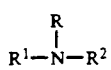

and b) 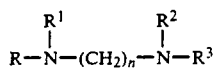

c) 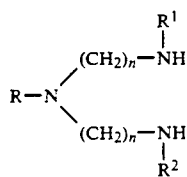

$n = 1-20$ where n is 1-20, R is $C_6-C_{20}$-alkyl and/or hydroxyalkyl $R^1$, $R^2$ and $R^3$ independently of one another are each hydrogen, lower alkyl, an alkyl or hydroxyalkyl radical corresponding to R or benzyl.

Depending on their properties, the fatty amines can be incorporated in the novel concentrates or solutions in the form of their salts, for example completely or partially as salts of carboxylic acids, such as acetic acid, propionic acid or 2-ethylhexanoic acid, with or without the addition of emulsifiers.

Examples of suitable fatty amines are dimethyl-$C_{10}$-$C_{18}$-alkylamines, in particular dimethyl-$C_{12}/C_{14}$-alkylamines, methyldioctylamine, methyldidecylamine, octyldiethanolamine, didodecyl-1,3-propylenediamine, $C_{13}/C_{15}$-alkyltrimethylenediamine, laurylpropylenediamine and N,N-bis-(3-aminopropyl)-laurylamine.

Furthermore, quaternary ammonium compounds or phosphonium compounds may be added.

A quaternary ammonium compound is, for example, a compound of the general formula $R^1R^2R^3R^4N^+Z^{31}$, where $R^1$ is alkyl of 8 to 20, in particular 12 to 20, carbon atoms or is benzyl which is unsubstituted or substituted by $C_1-C_{20}$-alkyl or halogen, $R^2$ is $C_1-C_{20}$-alkyl, $C_3-C_9$-alkoxyalkyl, EO or PO where n is from 1 to 50, $R^3$ is $C_1-C_6$-alkyl, $C_3$- or $C_4$-alkoxy or EO or PO where n is from 2 to 50, and $R^4$ is $C_1-C_{20}$-alkyl, or two of the radicals $R^1$ to $R^4$ together with the nitrogen atom form a heterocyclic radical which contains 4 or 5 carbon atoms, 1 or 2 nitrogen atoms and one, two or three double bonds, the carbon atoms being unsubstituted or substituted by $C_1-C_4$-alkyl or halogen, and Z is an acid radical.

Active phosphonium compounds which are particularly suitable are compounds of the formula

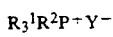

where $R^1$ is alkyl or hydroxyalkyl, each of 1 to 6 carbon atoms, or phenyl, $R^2$ is alkyl of 8 to 18 carbon atoms and Y is an acid radical, in particular a halide anion.

$R^1$ and $R^2$ are preferably straight-chain.

The quaternary phosphonium compounds may be present in the novel concentrates individually or as mixtures. Examples of such phosphonium compounds are trimethyl-n-dodecylphosphonium chloride, triethyl-n-decylphosphonium bromide, tri-n-propyl-n-tetradecylphosphonium chloride, trimethylol-n-hexadecylphosphonium chloride, tri-n-butyl-n-tetradecylphosphonium chloride, tri-n-butyl-n-dodecylphosphonium bromide, tri-n-butyl-n-decylphosphonium chloride, tri-n-butyl-n-hexadecylphosphonium bromide, tri-n-hexyl-n-decylphosphonium chloride, triphenyl-n-dodecylphosphonium chloride, triphenyl-n-tetradecylphosphonium bromide and triphenyl-n-octadecylphosphonium chloride.

It is also possible to add further fungicides, for example in emulsified form, such as N-tridecyl-2,6-dimethylmorpholine (tridemorph) and/or 4-(3-para-tert-butylphenyl)-2-methylpropyl-2,6-cis-dimethylmorpholine (fenpropimorph) and/or triazole and/or imidazole compounds, such as 1-(2-(2,4-dichlorophenyl)-4-methyl-1,3-dioxolan-2-ylmethyl)-1H-1,2,4-triazole, 1-(2-(2,4-dichlorophenyl)-1,3-dioxolan-2-ylmethyl)-1H1,2,4-triazole, 1-(2-(2,4-dichlorophenyl)-4-ethyl-1,3-dioxolan-2-ylmethyl)-1H-1,2,4-triazole, 1-(2-(2,4-dichlorophenyl)-4-propyl-1,3-dioxolan-2-ylmethyl)-1H-1,2,4-triazole (propiconazol), 1-(2-(2,4-dichlorophenyl)-4-pentyl-1,3-dioxolan-2-ylmethyl)-1H-1,2,4-triazole, 1-(2-(2,4-dichlorophenyl)-4-ethyl-1,3-dioxolan-2-ylmethyl)-1H-imidazole, α-tert-butyl-α-(p-chlorophenylethyl)-1H-1,2,4-triazol-1-yl-ethanol or 1-(β-alkoxy-2,4-dichlorophenethyl)-imidazole, and/or organotin compounds, in particular tributyltin (TBT) compounds, eg. TBT oxide, TBT versatoate, TBT benzoate, TBT naphthenate or TBT-HDO, and/or isothiazolinone compounds of the following formula

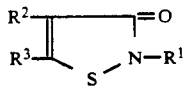

where $R^1$ is hydrogen, an alkyl, alkenyl or alkynyl radical of 1 to 18 carbon atoms, cycloalkyl having a $C_3-C_6$-ring and not more than 12 carbon atoms, or an aralkyl or aryl radical of not more than 19 carbon atoms and $R^2$ and $R^3$ independently of one another are each hydrogen, halogen or lower alkyl, or $R^2$ and $R^3$ form part of an aromatic radical.

In particular, the abovementioned fatty amines and their salts, quaternary ammonium/phosphonium compounds and, for example, other ionic and nonionic emulsifiers may be used as emulsifiers, with or without the addition of polar solvents.

In concentrated form, the water-dilutable agents contain the copper and/or zinc and/or cobalt and/or nickel in general in, for example, an amount of from 1 to 10% by weight, calculated as the element. Suitable concentrates contain, for example, from 2.5 to 50% of bis-(N-cycloalkyldiazeniumdioxy)-copper and/or -zinc and/or -nickel and/or -cobalt and/or bis-(N-alkyldiazeniumdioxy)copper and/or -zinc and/or -nickel and/or -cobalt and/or bis-(N-aryldiazeniumdioxy)copper and/or -zinc and/or -nickel and/or -cobalt, from 2.5 to 50% of a polymeric, complex-forming nitrogen compound, in particular a polyethyleneimine, from 0 to 40% of compounds having a fungicidal anion, from 0 to 20% of $C_6$–$C_{20}$-carboxylic acids, from 0 to 40% of a fatty amine and/or a fatty amine salt or a mixture thereof, from 0 to 40% of a quaternary ammonium compound or quaternary phosphonium compound and from 0 to 15% of tridemorph, fenpropimorph, triazole and/or imidazole derivatives, tributyltin compounds and/or isothiazolinone compounds, the sum being 100% by weight in each case, and, if necessary, minor amounts of other components, such as amines, ammonia, corrosion inhibitors and, if required, water and/or polar water-miscible solvents, the amounts of which may in general, however, be kept small and which essentially serve handling purposes.

However, the present invention also relates to the impregnation solutions of correspondingly low individual concentrations, which solutions can be prepared by dilution with water. The concentration for use is, for example, 0.01 to 0.50% by weight of metal, e.g. copper, in the aqueous impregnating solution, depending on the method of impregnation and the risk to the wood to be impregnated.

Dissolving the metal salts, in particular the copper and/or zinc compounds, in the polymeric, complex-forming nitrogen compounds, with or without the addition of water, gives highly concentrated water-soluble pastes and liquid concentrates which, after dilution with water, can be used to impregnate wood.

Highly concentrated water-soluble pastes and aqueous concentrates which can be used to impregnate wood, after being diluted with water, can be obtained by dissolving the metal salts, in particular copper and/or zinc compounds, in the polymeric, complex-forming nitrogen compounds, with or without the addition of water.

Impregnating solutions can be used to preserve wood on the one hand by manual methods, such as spraying, spreading, immersion or trough impregnation, or by large-scale industrial processes, for example the pressure impregnation process, pressure cycling process or double vacuum process. Wood is understood as meaning both solid wood and woodworking materials, eg. particle boards or plywood.

The wood preservative can be fixed in the wood, for example, under standard conditions, for example at from 5° to 35° C. in from 1 to 4 weeks, or by special methods, for example by treatment with superheated steam (at about 100°–150° C.) or by means of high frequency.

Fixing in drying chambers, for example at from 50° to 80° C. in from 12 to 24 hours, is also possible.

The pH of the aqueous impregnating solution is in general from 7.5 to 10.0. By adding acids, it is also possible, if required, to bring the solution to a pH of from below 7.5 to about 6.0.

The concentrates or solutions can be colored by water-soluble dyes or dye and/or pigment formations.

The amount of polymeric, complex-forming nitrogen compounds used in each case is such that it is both sufficient for complexing the metals, in particular the copper and/or zinc, and ensures penetration of the impregnating solution into the wood.

The Examples which follow illustrate the invention.

COMPARATIVE EXAMPLE A (not according to the invention)

25.0% of Cu-HDO
22.5% of diethylenetriamine
12.5% of nitrilotriacetic acid
40.0% of water The solution is diluted with water in a ratio of 2 parts of solution to 98 parts of water. Concentration for use: 2% in water.

In each case, 20 pine sapwood blocks (15×25×50 mm) were impregnated and

I. after fixing for 4 weeks at room temperature (20° C.)

II. after treatment with superheated steam for 1 h at 100° C. and a cooling time of 4 hours were washed thoroughly several times with water, the wash water was collected and the copper content was determined. The amount of copper washed out was expressed in relation to the total amount of copper in the wood before the washout process. No washout =0%, complete washout =100%.

Washout:
I. 15.5% of copper
II. 25.1% of copper

COMPARATIVE EXAMPLE B (not according to the invention)

13.5 % of K-HDO
6.25% of nitrilotriacetic acid
6.25% of boric acid
6.25% of diethylenetriamine
5.0 % of ethanolamine
4.0 % of $Cu(OH)_2CuCO_3$
58.75% of water
(corresponding to 12.5% of Cu-HDO)
Concentration for use: 4%
Washout:
I. 17.8% of copper
II. 28.5% of copper

COMPARATIVE EXAMPLE C (not according to the invention)

25.0% of Cu-HDO
17.5% of diethylenetriamine
5.0% of ethanolamine
12.5% of tartaric acid
12.5% of boric acid
27.5% of water
Concentration for use: 2%
Washout:
I. 6.5% of copper To determine the depth of penetration, pine palisades (length 1.20 m, diameter from 20 to 24 cm, end faces sealed with a coating, sapwood width more than 30 mm) were impregnated by the pressure impregnating process (reduced pressure for 1 hour, superatmospheric pressure for 2 hours). To determine the depth of penetration of the copper, impregnated timbers were cut open in the middle, the cut surfaces were treated with the monosodium salt of 4-pyrid-2-yl-azoresorcinol (monohydrate), which gives a red coloration with copper and the depth of penetration of the copper was measured. In general, 3 palisades were impregnated per test.

The following mean depths of penetration were determined:

| Cu penetration: | 10.5 mm | 12.0 mm | 9.8 mm |
|---|---|---|---|
| Mean sapwood width: | 37.2 mm | 35.1 mm | 40.0 mm |

COMPARATIVE EXAMPLE D (not according to the invention)

25.0% of bis-(N-phenyldiazeniumdioxy)copper
30.0% of dipropylenetriamine
12.5% of nitrilotriacetic acid
12.5% of boric acid
20.0% of water
Concentration for use: 2%
Washout:
I. 12.5% of copper
II. 24.1% of copper

EXAMPLES (according to the invention)

EXAMPLE 1

25% of Cu-HDO
19% of PEI, n about 100
56% of water
Concentration for use: 2.0%
Copper washout:
I. 4.2% of copper
II. 5.1% of copper
Copper penetration in pressure impregnation process: Pine palisades (reduced pressure for 1 hour, superatmospheric pressure for 2 hours): 35.2.mm, 38.5 mm, 32.1 mm The copper penetration is in agreement with the sapwood width and reaches the limit of the heartwood.

EXAMPLE 2

25% of bis-(N-phenyldiazeniumdioxy)copper
19% of PEI, n about 500
56% of water
Concentration for use: 2.0%
Copper washout:
I. 3.3% of copper
II. 4.5% of copper
Copper penetration in pressure impregnation process: 30.5 mm, 36.2 mm, 32.5 mm The copper penetration is in agreement with the sapwood width and reaches the limit of the heartwood.

EXAMPLE 3

25% of bis-($C_5$-$C_7$-alkyldiazeniumdioxy)copper
20% of PEI, n about 500
55% of water
Copper washout:
I. 5.5% of copper
Copper penetration in pressure impregnation process (palisade length 80 cm, diameter 18 cm): 30.7 mm The copper penetration is in agreement with the sapwood width and reaches the limit of the heartwood.

EXAMPLE 4

13.5% of K-HDO
7.5% of 2-ethylhexanoic acid
10.0% of PEI, n about 100
65.0% of water
4.0% of $Cu(OH)_2CuCO_3$
($\hat{=}$ 12.5% of Cu-HDO)
Concentration for use: 4%
Copper washout:
I. 3.6% of copper
II. 4.5% of copper
Copper penetration in pressure impregnation process: 35.5.mm, 32.0 mm, 40.1 mm The copper penetration is in agreement with the sapwood width and reaches the limit of the heartwood.

EXAMPLE 5

13.5 % of K-HDO
6.25% of 2-ethylhexanoic acid
6.25% of boric acid
11.25% of PEI, n about 50
4.0 % of $Cu(OH)_2CuCO_3$
58.75% of water
($\hat{=}$ 12.5% of Cu-HDO)
Concentration for use: 4%
Copper washout:
I. 6.1% of copper
II. 5.9% of copper
Copper penetration in pressure impregnation process: 31.1 mm, 37.8 mm, 35.0 mm The copper penetration is in agreement with the sapwood width and reaches the limit of the heartwood.

EXAMPLE 6

13.5% of K-HDO
5.0% of 2-ethylhexanoic acid
11.0% of PEI, n about 100
4.7% of copper borate
65.8% of water
Concentration for use: 4%
Copper washout:
I. 3.5% of copper
II. 4.0% of copper
Copper penetration in pressure impregnation process: 38.5 mm, 44.5 mm, 31.7 mm The copper penetration is in agreement with the sapwood width and reaches the limit of the heartwood.

EXAMPLE 7

13.5% of K-HDO
5.0% of 2-ethylhexanoic acid
5.0% of fluorophosphoric acid
12.5% of PEI, n about 500
4.0% of $Cu(OH)_2CuCO_3$
60.0% of water
Concentration for use: 4%
Copper washout:
I. 4.3% of copper
II. 3.8% of copper Copper penetration in pressure impregnation process (palisade length 80 cm, diameter 18.5 cm): 29.7 mm The copper penetration is in agreement with the sapwood width and reaches the limit of the heartwood.

EXAMPLE 8

13.5 % of K-HDO
6.25% of 2-ethylhexanoic acid
6.25% of boric acid
9.5 % of PEI, n about 100
3.00% of dipropylenetriamine
4.00% of $Cu(OH)_2CuCO_3$
57.50% of water
(≐ 12.5% of Cu-HDO)
Concentration for use: 4%
Copper washout:
I. 5.0% of copper
II. 5.0% of copper
Copper penetration in pressure impregnation process: 32.5 mm, 40.7 mm, 37.5 mm The copper penetration is in agreement with the sapwood width and reaches the limit of the heartwood.

EXAMPLE 9

13.5 % of K-HDO
6.25% of 2-ethylhexanoic acid
6.25% of boric acid
8.5 % of PEI, n about 100
5.0 % of polyamidoamine
4.0 % of $Cu(OH)_2CuCO_3$
56.5 % of water
Concentration for use: 4%
Copper washout:
I. 4.8% of copper
II. 5.6% of copper
Copper penetration in pressure impregnation process (palisade length 80 cm, diameter 18.5 cm): 28.7 mm The copper penetration is in agreement with the sapwood width and reaches the limit of the heartwood.

EXAMPLE 10

18.25% of a condensate of triethanolamine and diethylenetriamine in a ratio of 1:1
13.50% of K-HDO
6.25% of boric acid
4.00% of $Cu(OH)_2CuCO_3$
58.00% of water
(≐ 12.5% of Cu-HDO)
Concentration for use: 4%
Copper washout:
I. 6.7% of copper
II. 5.9% of copper

EXAMPLE 11

13.5% of K-HDO
18.0% of 2-ethylhexanoic acid
10.5% of dimethylalkylamine ($C_{12}$–$C_{14}$)
9.5% of N,N-bis-(3-aminopropyl)-laurylamine
0.0% of PEI, n about 100
4.0% of $Cu(OH)_2CuCO_3$
4.5% of water
(- 12 5% of Cu-HDO)
Concentration for use: 2.5%
Copper washout:
I. 5.5% of copper
II. 6.0% of copper

EXAMPLE 12

8.4% of K-HDO
0.0% of 2-ethylhexanoic acid
6.7% of PEI, n about 100
2.7% of $Cu(OH)_2CuCO_3$
0.0% of dimethylalkylamine ($C_{12}$–$C_{14}$)
6.7% of tridemorph
0.0% of ethoxylated coconut fatty amine (density 0.96 g/cm$^3$ at 50° C.)
Concentration for use: 4%
Copper washout:
I. 2.5% of copper
II. 2.6% of copper

EXAMPLE 13

8.4% of K-HDO
0.0% of 2-ethylhexanoic acid
6.7% of PEI, n about 100
2.7% of $Cu(OH)_2CuCO_3$
10.0% of dimethylalkylamine ($C_{12}$–$C_{14}$)
6.7% of fenpropimorph
10.0% of ethoxylated coconut fatty amine (density 0.96 g/cm: at 50° C.)
3.5% of ethoxylated nonylphenol, about 10 EO units
2.0% of water
Concentration for use: 4%
Copper washout:
I. 1.5% of copper
II. 2.0% of copper

EXAMPLE 14

8.4% of K-HDO
5.0% of 2-ethylhexanoic acid
6.7% of PEI, n about 100
2.7% of $Cu(OH)_2CuCO_3$
16.7% of N-benzyl-N-($C_{12}$–$C_{14}$)-alkyl-N,N-dimethylammonium chloride
60.5% of water
Concentration for use: 4%
Copper washout:
I. 2.5% of copper
II. 2.7% of copper

EXAMPLE 15

13.5% of K-HDO
9.0% of PEI, n about 100
5.0% of 2-ethylhexanoic acid
4.0% of $Cu(OH)_2CuCO_3$
5.0% of propiconazol
12.5% of ethoxylated nonylphenol about 15 EO units
2.5% of propylene glycol
62.0% of water
Concentration for use: 4%
Copper washout:
I. 3.5% of copper
II. 4.9% of copper

We claim:
1. A wood preservative composition, comprising:
   an effective preservative amount of a metal compound of an N-organyldiazeniumdioxy compound and a complex forming
2. The preservative of claim 1, wherein said N-organoyldiazeniumdioxy compound is bis-(N-cyclohexyldiazeniumdioxy) copper.
3. A process for preserving wood, which comprises: treating said wood with a preserving effective amount of the preservative composition of claim 1.

* * * * *

UNITED STATES PATENT AND TRADEMARK OFFICE
CERTIFICATE OF CORRECTION

PATENT NO. : 5,187,194

DATED : February 16, 1993

INVENTOR(S) : Goettsche et al.

It is certified that error appears in the above-identified patent and that said Letters Patent is hereby corrected as shown below:

Column 10, line 58, Claim 1:

should read --1. A wood preservative composition, comprising: an effective preservative amount of a metal compound of an N-organyldiazeniumdioxy compound and a complex forming polyethyleneimine having a polymerization degree of 50 to 1000.--

Signed and Sealed this

Ninth Day of May, 1995

Attest:

BRUCE LEHMAN

*Attesting Officer*  *Commissioner of Patents and Trademarks*